(12) United States Patent
Sawyer

(10) Patent No.: US 7,343,030 B2
(45) Date of Patent: Mar. 11, 2008

(54) DYNAMIC TUMOR TREATMENT SYSTEM

(75) Inventor: Timothy E. Sawyer, Boise, ID (US)

(73) Assignee: ImQuant, Inc., Boise, ID (US)

( * ) Notice: Subject to any disclaimer, the term of this patent is extended or adjusted under 35 U.S.C. 154(b) by 592 days.

(21) Appl. No.: 10/910,711

(22) Filed: Aug. 3, 2004

(65) Prior Publication Data

US 2005/0041843 A1 Feb. 24, 2005

Related U.S. Application Data

(60) Provisional application No. 60/534,633, filed on Jan. 7, 2004, provisional application No. 60/508,117, filed on Oct. 2, 2003, provisional application No. 60/492,796, filed on Aug. 5, 2003.

(51) Int. Cl.
*G06K 9/00* (2006.01)
(52) U.S. Cl. ............. 382/128; 382/131; 382/199; 378/65; 378/901; 600/410
(58) Field of Classification Search ............. 382/118, 382/128, 131, 294, 132, 199; 378/65, 98.9, 378/901; 600/411, 426, 439, 407, 431, 410, 600/436, 414, 415, 1, 429
See application file for complete search history.

(56) References Cited

U.S. PATENT DOCUMENTS

| | | | |
|---|---|---|---|
| 4,736,307 A | 4/1988 | Salb | |
| 5,317,616 A * | 5/1994 | Swerdloff et al. | 378/65 |
| 5,373,844 A | 12/1994 | Smith et al. | |
| 5,418,827 A | 5/1995 | Deasy et al. | |
| 5,661,773 A | 8/1997 | Swerdloff et al. | |
| 5,724,400 A * | 3/1998 | Swerdloff et al. | 378/65 |
| 5,740,802 A | 4/1998 | Nafis et al. | |
| 5,859,891 A | 1/1999 | Hibbard | |
| 5,868,673 A | 2/1999 | Vesely | |
| 5,871,018 A | 2/1999 | Delp et al. | |
| 6,067,372 A | 5/2000 | Gur et al. | |
| 6,104,779 A | 8/2000 | Shepherd et al. | |
| 6,112,112 A | 8/2000 | Gilhuijs et al. | |
| 6,167,296 A | 12/2000 | Shahidi | |
| 6,222,544 B1 | 4/2001 | Tarr et al. | |
| 6,226,352 B1 | 5/2001 | Salb | |
| 6,236,875 B1 | 5/2001 | Bucholz et al. | |
| 6,239,724 B1 | 5/2001 | Doron et al. | |
| 6,258,104 B1 | 7/2001 | Kreizman et al. | |
| 6,292,578 B1 | 9/2001 | Kalvin | |
| 6,335,980 B1 | 1/2002 | Armato, III et al. | |
| 6,347,240 B1 | 2/2002 | Foley et al. | |
| 6,398,710 B1 | 6/2002 | Ishikawa et al. | |
| 6,422,748 B1 | 7/2002 | Shepherd et al. | |
| 6,434,415 B1 | 8/2002 | Foley et al. | |
| 6,470,207 B1 | 10/2002 | Simon et al. | |
| 6,546,073 B1 | 4/2003 | Lee | |
| 6,556,695 B1 | 4/2003 | Packer et al. | |
| 6,631,284 B2 * | 10/2003 | Nutt et al. | 600/427 |
| 6,661,870 B2 * | 12/2003 | Kapatoes et al. | 378/65 |

(Continued)

*Primary Examiner*—Sheela Chawan
(74) *Attorney, Agent, or Firm*—Quarles & Brady LLP

(57) ABSTRACT

A workstation imports medical images that depict a tumor and provides tools that enable a physician to see the results of prior therapies, plan future therapies, predict the outcome of future therapies and control future therapies. The workstation processes the imported images to produce isonumeric images of the tumor that can be analyzed and output to therapeutic systems.

17 Claims, 5 Drawing Sheets

U.S. PATENT DOCUMENTS

| | | |
|---|---|---|
| 6,669,635 B2 | 12/2003 | Kessman et al. |
| 6,675,810 B2 | 1/2004 | Krag |
| 6,681,129 B2 | 1/2004 | Matsuzaki et al. |
| 6,694,057 B1 | 2/2004 | Miller et al. |
| 6,751,290 B2 * | 6/2004 | Salb .......................... 378/98.9 |
| 2001/0022853 A1 * | 9/2001 | Takaoka ..................... 382/167 |
| 2003/0211036 A1 | 11/2003 | Degani et al. |

* cited by examiner

DYNAMIC TUMOR TREATMENT SYSTEM

CROSS-REFERENCE TO RELATED APPLICATIONS

This application claims the benefit of U.S. Provisional patent application Ser. No. 60/492,796 filed on Aug. 5, 2003 and entitled "Method For Generation Of Exportable Three-Dimensional Tumor Volumes From Radiographic Images And Other Digital Systems, And Real-Time Incorporation Of These Volumes Into Biopsy, Endoscopy, Surgery, Radiation Therapy Planning, and Radiation Therapy Delivery Guidance"; U.S. Provisional patent application Ser. No. 60/508,117 filed on Oct. 2, 2003 and entitled "System For The Incorporation Of Intra-Operative Data Into Three-Dimensional Volumes Used As Targets During Surgical Guidance, And For The Mathematical Analysis Of Three-Dimensional Target Volumes," and U.S. Provisional patent application Ser. No. 60/534,633 filed Jan. 7, 2004 and entitled "Software And Hardware Integrating The Isonumeric Volume-Based Imaging Format In An Oncology Patient-Management Workstation, For Rapid Response Assays With Or Without Image Creation, For Software Facilitating Dynamic Chemotherapy Administration, For Image Interpretation And Analysis, And For Advanced Real-Time Image Guidance In Soft Tissue."

BACKGROUND OF THE INVENTION

The field of the invention is medical imaging, and particularly, the use of medical imaging in the treatment of cancer.

Advanced imaging techniques for brain and other neoplasms acquire a variety of physiological data in addition to anatomic data. These include PET scanning, conventional MRI, MRI-spectroscopy, diffusion imaging, SPECT, perfusion imaging, functional MRI, tumor hypoxia mapping, angiogenesis mapping, blood flow mapping, cell death mapping and other methods. In addition, it is anticipated that new and better agents for use in SPECT, PET, and other imaging will be created and/or identified. These techniques will lead to an improvement in the ability to differentiate tumor from normal tissue.

Traditional display of physiologic images is in several ways insufficient. Physiologic images generated from sources such as PET and SPECT are indistinct (tumors have "blurry" borders), and are anatomically ambiguous. Fusion software has facilitated the viewing of neoplasms represented by PET and SPECT within the context of anatomic detail represented by CT. Integrated PET-CT and SPECT-CT devices have improved registration and fusion of anatomic and physiologic images. Traditionally, fused images are viewed by fading between CT and physiologic images, ranging from 0% CT/100% physiologic images, to 100% CT/0% physiologic images.

In present day treatment planning the creation of a three-dimensional treatment volume often involves the manual, slice-by-slice digital outlining of tumor on sequential tomographic images at a computer workstation. Computers are then used to convert cut-by-cut digital outlines into three-dimensional volumes, which become targets for surgical and/or radiation therapy planning. This process is labor-intensive. More importantly, however this process relies on the judgment of the person, usually a physician, digitizing the slice-by-slice images.

There are several limitations associated with the reliance on human judgment in this capacity. First, different physicians have different levels of experience in interpreting scans. Planning based on volumes generated by inexperienced physicians will be less accurate. Secondly, even for experienced physicians, interpretation of imaging findings is in many cases difficult, and in many instances based on "best guess" decision making. Even for experienced physicians, there will always be inter-observer variability. Thus, in research/protocol situations, outcomes data will not be directly transferable from institution to institution.

For imaging modalities such as spectroscopy or PET, particularly for tumors that invade adjacent structures or soft tissues, the line between tumor and adjacent non-tumorous structures is subjective and indistinct. This creates variability from cut to cut, patient to patient, and physician to physician. More importantly, however, it creates uncertainty with regard to the optimal volume needed to maximize local control while minimizing dose (and damage) to adjacent structures.

Traditional systems that display images or incorporate images into treatment processes consider images as physiologically homogenous. This is despite the fact that tumors are known to be physiologically heterogeneous. The limitations described above, related to display of a tumor's outer boundary, also apply to display of a tumor's internal heterogeneity.

SUMMARY OF THE INVENTION

The present invention is a method and system for analyzing images of tumors for the purpose of diagnosis and treatment planning. More specifically, the system imports images that depict a tumor, produces isonumeric images from such imported images which clearly indicate the boundary of a selected tumor parameter threshold, stores the isonumeric images for continued use and analysis, and analyzes isonumeric images produced during the treatment process.

The tumor contour depicted in an isonumeric image has broad applicability to physiologic imaging techniques, including MRI, MR Spectroscopy (MRS), MRS Imaging (MRSI), perfusion imaging, additional functional MR techniques, PET, SPECT, and many other imaging processes. The combination of the isonumeric contour images, and mathematical methods designed to analyze relationships between and changes in sets of isonumeric contours is superior to traditional methods of displaying images, and interpreting images. In addition, isonumeric images can be directly integrated into the processes of targeting external beam irradiation and brachytherapy, planning cancer surgery, guiding cancer surgery, and predicting and measuring the response to radiation therapy and systemic therapy (included but not limited to chemotherapy and hormonal therapy). A three-dimensional isonumeric contour image can be exported to therapeutic systems and to surgery guidance systems.

By employing multiple thresholds, the isonumeric image depicts a corresponding plurality of 3D surface contours that define multiple tumor volumes. Larger volumes include areas peripheral to the center of the tumor, areas that should in theory contain lower concentrations of tumor cells. Smaller volumes on the other hand contain larger concentrations of tumor cells. Use of multiple volumes generated from the same image set is very useful in determining therapeutic ratios during radiation therapy planning (if dose-volume histograms for normal structures adjacent to tumor are particularly favorable, a radiation oncologist may decide to prescribe to a larger volume), and surgical guidance (a surgeon may decide to remove a lesser or greater volume of tissue during glioblastoma resection, depending on the relationship between the volumes and critical anatomic or functional areas).

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

The present invention may be implemented in a number of different ways. In the preferred embodiment it is implemented in a stand-alone computer workstation; however, it can be appreciated that some or all of the functions may be carried out in other systems such as imaging systems, PAC systems or therapeutic systems.

Figure 1:
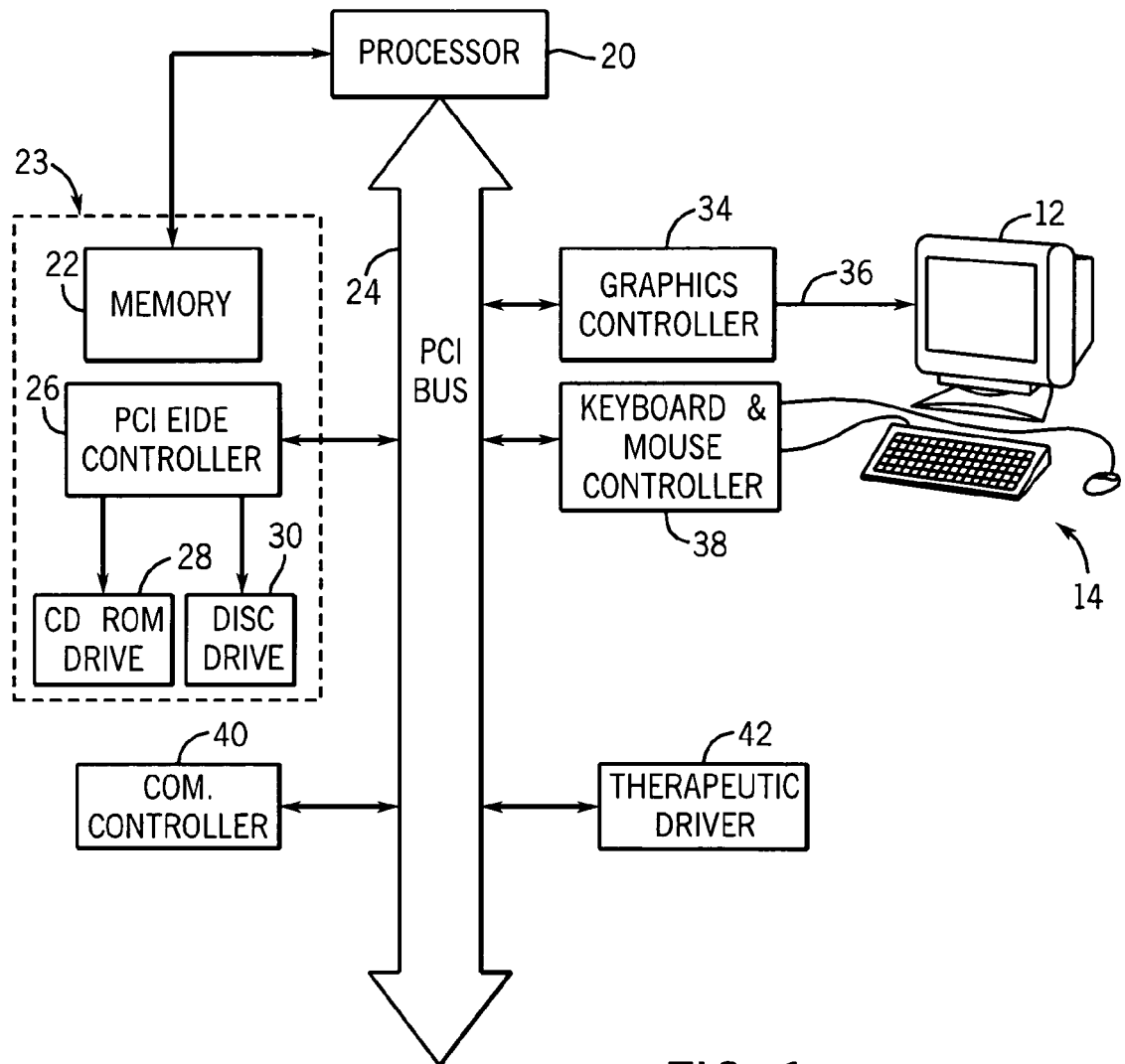
FIG. 1 is a block diagram of a workstation which is programmed to practice the preferred embodiment of the invention.

Referring particularly to FIG. 1, the computer workstation includes a processor 20 which executes program instructions stored in a memory 22 that forms part of a storage system 23. The processor 20 is a commercially available device designed to operate with one of the Microsoft Corporation Windows operating systems. It includes internal memory and I/O control to facilitate system integration and integral memory management circuitry for handling all external memory 22. The processor 20 also includes a PCI bus driver which provides a direct interface with a 32-bit PCI bus 24.

The PCI bus 24 is an industry standard bus that transfers 32-bits of data between the processor 20 and a number of peripheral controller cards. These include a PCI EIDE controller 26 which provides a high-speed transfer of data to and from a CD ROM drive 28 and a disc drive 30. A graphics controller 34 couples the PCI bus 24 to a CRT monitor 12 through a standard VGA connection 36, and a keyboard and mouse controller 38 receives data that is manually input through a keyboard and mouse 14.

The PCI bus 24 also connects to a communications controller 40. The controller 40 connects to an intranet that links the workstation to one or more imaging systems, a department PAC system, or an institution image management system. Images may be downloaded to the workstation from any source connected to the intranet, from the internet, or from a CD.

Optionally, the PCI bus 24 may also connect to a therapeutic system through a therapeutic driver card 42. As will be described below, computer data may be output through the therapeutic driver to program a therapeutic system to treat a patient, or may be downloaded to CD.

Figure 2:
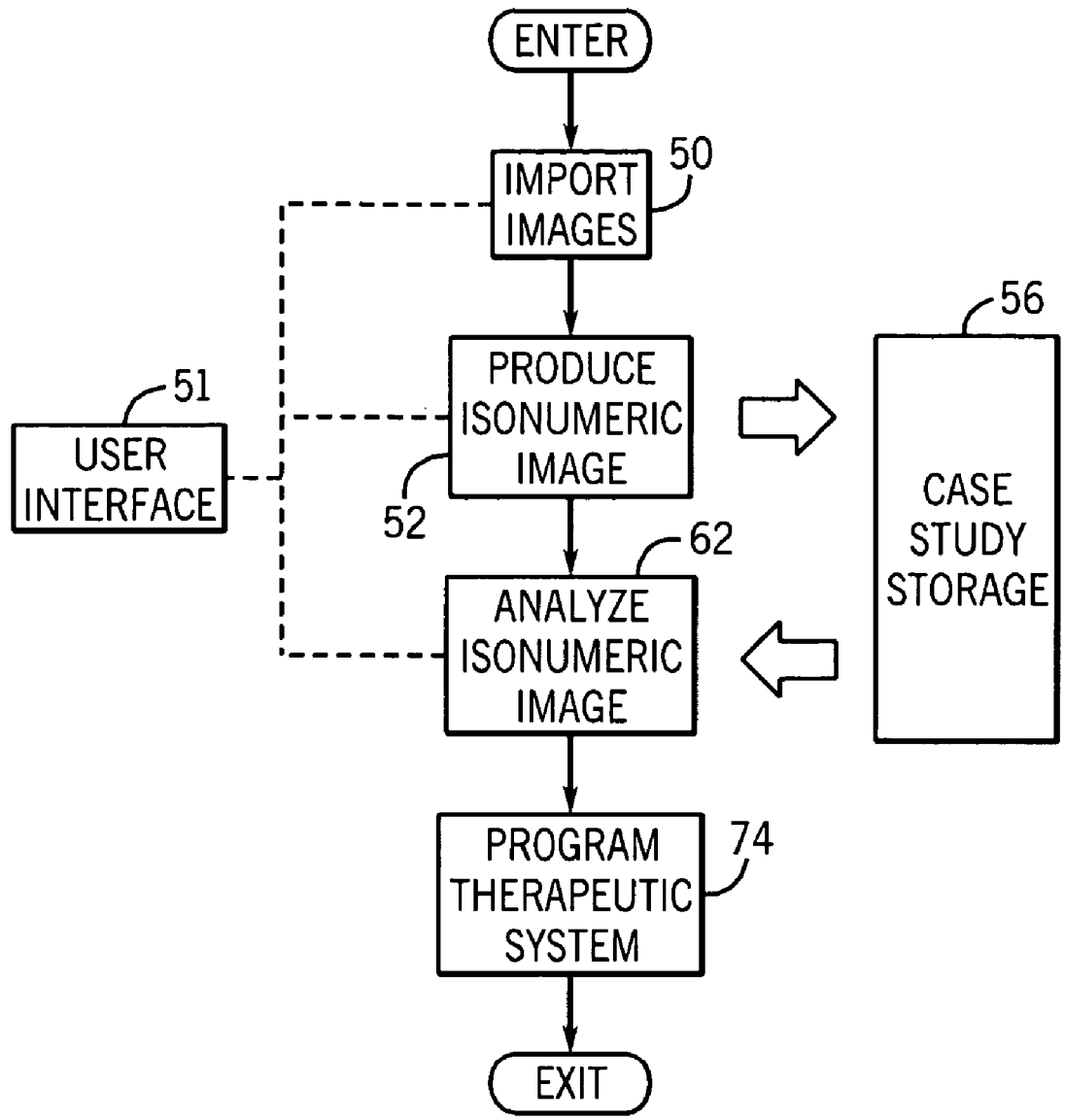
FIG. 2 is a flow chart of the software executed by the workstation of FIG. 1 to practice the present invention.

The dynamic tumor treatment system can be configured to perform a number of different functions in the treatment of cancer. The configuration of the system and its operation are controlled through a user interface module 51 that prompts the user with information that is output to display 12 and receives user information input through the keyboard and mouse 14. In the first preferred embodiment the system is configured for radiation therapy planning as shown in FIG. 2. In this configuration images may be imported from various sources connected to the Intranet as indicated at process block 50. These may include MR images, x-ray CT images, PET images, SPECT images or MR spectroscopy images. Images are registered for display with a system coordinate system. This enables images from different sources or different times during treatment to be imported and aligned with each other. Such registration may use fixed points in the acquired image or fiducials that are implanted in the patient for this purpose. Typically, an image modality is chosen that will contrast the particular tumor with surrounding tissue or that measures a parameter that characterizes the tumor. As an example, in FDG-PET imaging, radiolabelled glucose is preferentially taken up by tumor cells. As another example, ProstaScint binds to PSMA (prostate specific membrane antigen), which is overexpressed in prostate cancer. Other non-image clinical data regarding the patient may also be imported for use in later analysis. As an example, for the prostate cancer surgical planning application described later in this document, ProstaScint-based isonumeric contour data, the serum PSA value, the biopsy Gleason score value, and the clinical stage can be combined in a prognostic factor model used to predict the likelihood of extra-capsular extension or cavernous nerve involvement. As another example, for using changes in isonumeric contours and contour relationships to predict the likelihood of lung cancer complete response to chemotherapy, factors such as tumor histology and tumor grade can be integrated into the predictive models.

Figure 5A:
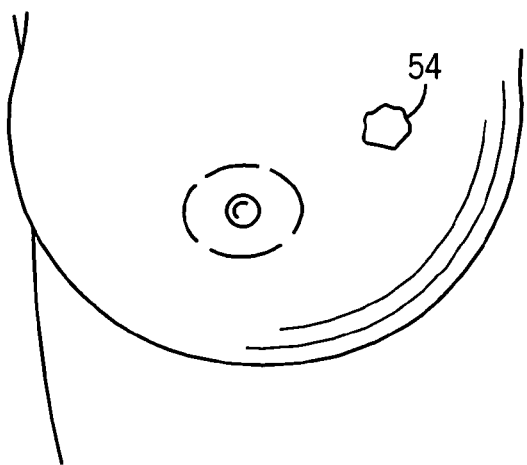
FIGS. 5A-5C are exemplary isonumeric images produced by the workstation of FIG. 1.
Figure 5B:
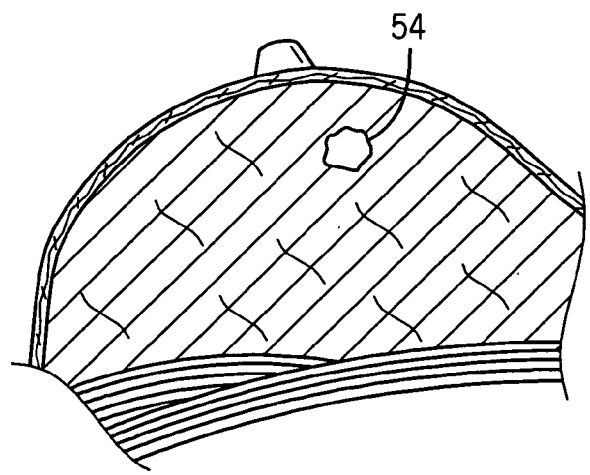
Figure 5C:
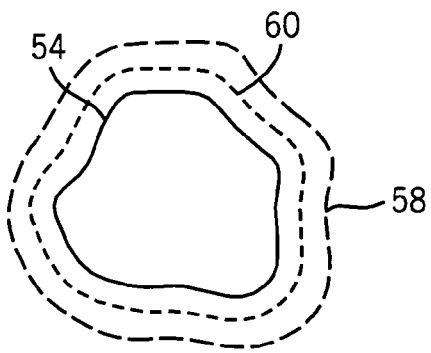

As indicated at process block 52 a second step is to produce an isonumeric image using the imported images. As will be discussed in more detail below, an isonumeric image is comprised of one or more contours which indicate a selected threshold level of a measured tumor parameter in the image. For example, the parameter may be FD-glucose uptake in a PET image, and the selected intensity level is a threshold of gamma radiation level which indicates the presence of a tumor in the human breast. The isonumeric contour can be viewed as a three-dimensional, closed contour surface which defines a boundary in three-dimensional space, or it can be viewed as a two-dimensional, open or closed contour line which defines a boundary in two-dimensional space. A set of three-dimensional isonumeric contours, of varying threshold values, can be sliced to form a series of two-dimensional contour lines. As shown in FIGS. 5A and 5B, an isonumeric contour line 54 may be displayed on the anatomical image to indicate where in the anatomy the tumor is located. As shown in FIG. 5C, the same isonumeric contour line 54 can be displayed separately from the anatomy in much larger scale in order to better see the details of its shape.

The treatment of cancer is an iterative process in which a therapy is repeatedly employed and the tumor is repeatedly imaged and analyzed. These acquired images and their corresponding isonumeric images are stored in a case study storage 56. As shown in FIG. 5C, the isonumeric images from a series of such images may be registered with each other and displayed to reveal and analyze the results of the therapy. In the example shown in FIG. 5C, the tumor has shrunk in size from an initial acquisition indicated by dashed line 58 and a first treatment indicated by dotted line 60. By storing the case history as a series of isonumeric images, the results of the treatments can thus be easily seen and analyzed.

Figure 4:
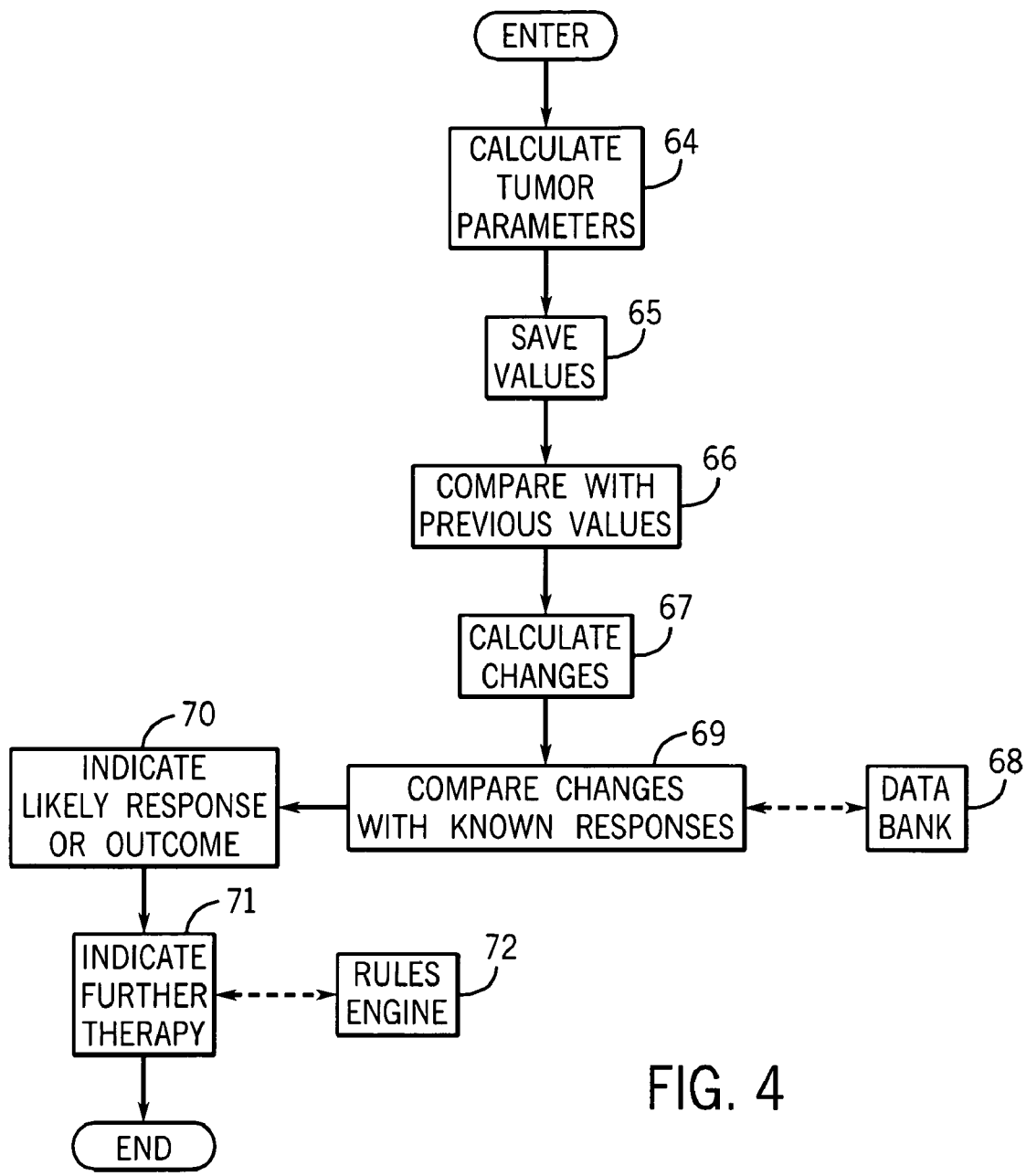
FIG. 4 is a flow chart of the method for analyzing the isonumeric image which forms part of the software of FIG. 2; and making treatment recommendations based on the analysis.

As indicated in FIG. 2 by process block 62, the acquired isonumeric image may be analyzed to produce information that is valuable in recommending or planning further treatment. This step is shown in more detail in FIG. 4. More specifically, characteristics related to the tumor as defined by the isonumeric contour image, including characteristics of individual contours and characteristics related to relationships between contours, are calculated at process block 64. These may include the following: calculate volume of each contour; calculate surface area of each contour; calculate shape characteristics; calculate median, mean, peak intensity values for voxels confined within a contour-defined volume; calculate contour distances from reference points or center; calculate distances of contours from each other; calculate volumes of contours containing contours of progressively increasing intensity ("elevations"); calculate volumes of contours containing contours of progressively decreasing intensity ("depressions"); calculate differences in threshold intensity levels, maximum or minimum intensity level within elevation or depression, versus contour representing base of depression or elevation; calculate locations of depressions and elevations; and calculate range or average thickness of contours. These are only a sampling of the calculations that may be made employing the isonumeric images. All the calculated values are stored in the case study storage as indicated at process block 65.

The numbers, sets of numbers, graphs, and equations representing pre-therapy isonumeric contours or contour sets stored in case study storage 56, can then be compared to numbers, sets of numbers, graphs, or equations from post-therapy images, as indicated at process block 66. In response to therapy (such as chemotherapy or radiation therapy) a tumor's physiology may change significantly, without a significant change in the size, surface area, or shape of a contour representing only the tumor's outer boundary, especially early in therapy. Therefore, numeric and morphologic parameters of multiple isonumeric contours within an image, as well as the numeric and spatial relationships between such isonumeric contours within an image, can be analyzed. The results of such an analysis can be represented by a number, a set of numbers, graphs, or equations.

The changes can be calculated as indicated at process block 67 and represented by separate numbers, groups of numbers, graphs, and equations. As indicated at process block 69, these changes, in turn, are compared to changes in a data bank 68 of changes for which the extent of response, ultimate degree of response, or clinical outcome is known. As indicated by process block 70, the extent of response or likelihood of complete response or other favorable clinical outcome, can then be indicated, in percentage terms or by response category (i.e. progression, no response, minimal response, moderate response, complete response).

As indicated at process block 71 the system will also recommend changes in therapy based on the comparison of isonumeric images acquired at different stages of treatment. Such recommendations are based on rules which are stored in a rules engine 72 and the recommendation is indicated on the display 12. The rules engine stores a plurality of rules that relate measured changes in the tumor parameters calculated above to suggested further therapy. The rules are of the form: For [tumor type], if [number] [treatment type] treatments have been performed and change in [calculated tumor parameter change name] is [<=>number], then indicate [message]. They are sorted by tumor type such that only those rules for the particular tumor type in question are tested. If a rule tests true, then the indicated treatment suggestion message is displayed.

As an example, breast cancer can be treated in a neoadjuvant fashion (chemotheapy prior to surgical resection). Isonumeric contours from PET imaging prior to treatment initiation may be compared to isonumeric contours from PET images obtained just prior to cycle two of chemotherapy. If this comparison reveals that the degree of response to chemotherapy, or the likelihood of complete response to therapy, is low, different chemotherapy agents could be recommended for cycle two of chemotherapy. Alternatively, the patient could proceed directly to surgery. As a second example, one cycle of chemotherapy could be administered just prior to resection of a brain glioblastoma multiform. Isonumeric contours from MRI images obtained prior to chemotherapy administration could be compared to those from MRI images obtained a few days after chemotherapy administration, just prior to resection. If the analysis reveals that the tumor is minimally sensitive to the chemotherapy, different chemotherapy could be recommended adjuvantly (post-operatively). As a third example, isonumeric contours from physiologic images obtained prior to radiation therapy administration could be compared to isonumeric contours obtained mid-way through a multi-week course of radiation therapy. If the analysis reveals a significant response to radiation therapy, or a high likelihood of complete response, the total radiation therapy dose could be reduced. In performing this analysis it is important to understand that the absolute values of voxel intensity values used to produce an isonumeric image are related to many factors, including but not limited to dose of imaging contrast agent administered, time between contrast agent administration and image acquisition, duration of image acquisition, baseline metabolic rate, body water content, and oral intake prior to imaging. If imaged twice in rapid succession, for example, a particular area in a tumor may therefore be represented by two different absolute voxel intensity values or isonumeric contours. Isonumeric contours should therefore be mathematically normalized prior to analysis to take into account such variables.

Referring again to FIG. 2, the final step in the process is to determine the subsequent therapy as indicated at process block 74. This includes using the results of the above-described analysis to automatically recommend a modification in the next chemotherapy cycle's drugs, doses, or intervals, to increase or decrease the planned radiation therapy dose; or to proceed to surgery. In some cases, an output image of the tumor volume is provided, such as for modification of the radiation therapy field borders, or to serve as a surgical dissection plane. The output image may contain all isonumeric contours within the range of voxel intensity values comprising that image. Alternatively, the user may select one or a series of threshold values of internal isonumeric contours (contours inside of the outer boundary contour) to be displayed, using one of several methods outlined below. This is particularly relevant in three clinical scenarios. First, if the diagnostic system to be programmed is used purely for image display, it may be helpful to have only a few isonumeric contours shown, so that if overlaid upon an anatomic image, anatomic details can still be appreciated. Second, the output image may be conveyed through the therapeutic drive circuit 42 to a radiation therapy system such as that disclosed in U.S. Pat. No. 5,418,827 issued on May 23, 1995 and incorporated herein by reference. The radiation therapy system registers the output image with its coordinate system reference and the patient, and then uses the isonumeric output image of the tumor to produce a set of dose maps which indicate the treatment level in a corresponding set of slices through the tumor. By producing an isonumeric output image having a plurality of contour surfaces corresponding to a plurality of different threshold values of particular mathematical or clinical significance, the contours serve as "internal borders" to guide the differential delivery of radiation doses across the tumor or organ being targeted. As an example, based on internal isonumeric contours, intensity modulated techniques may be used to deliver high radiation therapy doses to contour-defined high risk areas, and low doses to contour-defined low risk areas, particularly if these low risk areas are located adjacent to critical structures. Similarly, high-risk areas as defined by contours may be given an extra "boost" of stereotactically delivered radiation therapy, once conventional radiation therapy delivery is complete.

Figure 6:
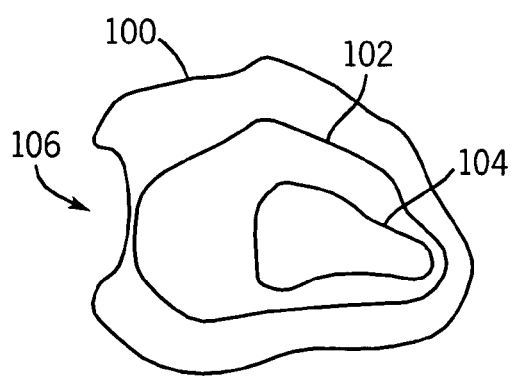
FIG. 6 is a display of a slice taken through an exemplary 3D isonumeric image with three contours.

As shown in FIG. 6, for example, three isonumeric contour lines 100, 102 and 104 are displayed for a particular slice through a tumor. The contour 102 corresponds to the measured boundary of the tumor at this slice location which requires a normal dose, and contour 104 indicates the boundary of a high-risk part of the tumor which requires a higher dose. The contour 100 defines a region around the tumor which is prescribed a lighter dose, and this isonumeric contour 100 has been manually altered at 106 to avoid harming critical tissues. Analysis of changes in contours and contour patterns during a multiple-week course of radiation therapy, along with comparison of these changes to a data bank of changes for which the ultimate degree of response and long-term control is known, can lead to recommendations for mid-treatment alterations in the prescription of differential dose across a tumor or organ target. Third, the display of contours according to mathematical and clinical significance may help determine therapeutic ratios related to surgery and radiation therapy. It may make sense in the case of a glioblastoma multiform, for example, to use contours to define high-risk, intermediate high-risk, intermediate-low risk, and low risk areas, to be approached with surgery, stereotactic radiosurgery, high-dose fractionated intensity modulated radiation therapy, and low-dose fractionated intensity modulated radiation therapy, respectively.

The output image used to determine or control subsequent therapy is often the most recent isonumeric contour image produced at one or more threshold values as in FIG. 5C or the isonumeric image may be superimposed on the anatomic image as in FIGS. 5A and 5B. As a result of the analysis, however, the isonumeric image may also be modified before being output, or may be placed in a format that will allow modification in a separate therapeutic system (such as DICOM-RT). Such modification may be done by manually redrawing the tumor boundary or the modification may be done automatically by changing the threshold level. For example, the most recently produced isonumeric image may indicate the current boundary of a malignant tumor, but the threshold level used to produce that isonumeric image may be reduced in order to increase the size of the tumor boundary in the output image. This may be done to increase the size of the treatment region. On the other hand, changes may be made over portions of the isonumeric boundary image to avoid damaging critical tissues during therapy. This is particularly necessary when treating brain tumors and prostate tumors.

It should be apparent that while the isonumeric images have been described herein for use in a radiation therapy system, these images also have other useful applications. For example, the isonumeric images may be output to an image guided surgery system which registers the isonumeric contour(s) with a real-time imaging system used by a surgeon. Similarly, it can be used for real-time guidance of other local procedures, such as cryotherapy, radiofrequency ablation, therapeutic ultrasound, and image-guided biopsy. Isonumeric contours can also be used to choose the imaging source to be used for guidance or targeting. As an example, the degrees of overlap and underlap of selected contours from two separate imaging sources performed at the same point in the therapeutic course can be calculated. Based on these calculated values, the user may decide to use images from one imaging source, to use images from the other imaging source, or to use contours from both imaging sources. The system described herein is capable of forming composite target volumes from two or more contours and from two or more imaging sources.

Isonumeric contours can also be used for the application of surgical planning. In the preferred embodiment surgical planning is implemented in the stand-alone computer workstation used to create the isonumeric contours. As an example, ProstaScint images, in the form of isonumeric contours, of a prostate containing prostate cancer can be viewed overlaid upon anatomic (such as CT) images of the prostate gland. The anatomic location of neural structures critical to sexual potency are digitized on a slice by slice basis. The slices are converted to a volume, using standard techniques used in most radiation therapy planning and surgical guidance systems. The relative locations of the nerves and the tumors within the prostate gland, as defined by isonumeric contours, are displayed. The distance of the isonumerically-defined tumor from the nerves is calculated. The quantity of tumor in the proximity of the nerves is quantified, based on the volume of the contour containing tumor and the relative intensity of the tumor relative to normal prostate baseline. If desired, the distance and tumor quantification values can be compared to values in a data bank of values for which the pathologic relationship between tumor and nerve is known. The surgeon can then make a decision with regard to the appropriate level of aggressiveness in dissecting prostate from nerve during prostatectomy.

Images made up of multiple isonumeric contours can also be used in diagnosis. Mathematical parameters related to individual contours comprising a tumor or suspected tumor, or related to the relationships between multiple contours comprising a tumor or suspected tumor, can be expressed as numbers, sets of numbers, graphs, or equations. These numbers, sets of numbers, graphs, or equations can be compared to numbers, sets of numbers, graphs, or equations in a case study storage bank for which the diagnoses have been established. Based on these comparisons, a rank order list of differential diagnoses can be established (with percent likelihood's). Alternatively, isonumeric images can be directly compared to isonumeric images in a case study storage bank for which the diagnosis has been established.

Finally, changes in isonumeric contours or isonumeric contour sets following administration of small doses of a therapeutic agent can be calculated, and compared to changes in contours or contour sets in a case study storage bank for which the diagnosis has been established.

Figure 3:
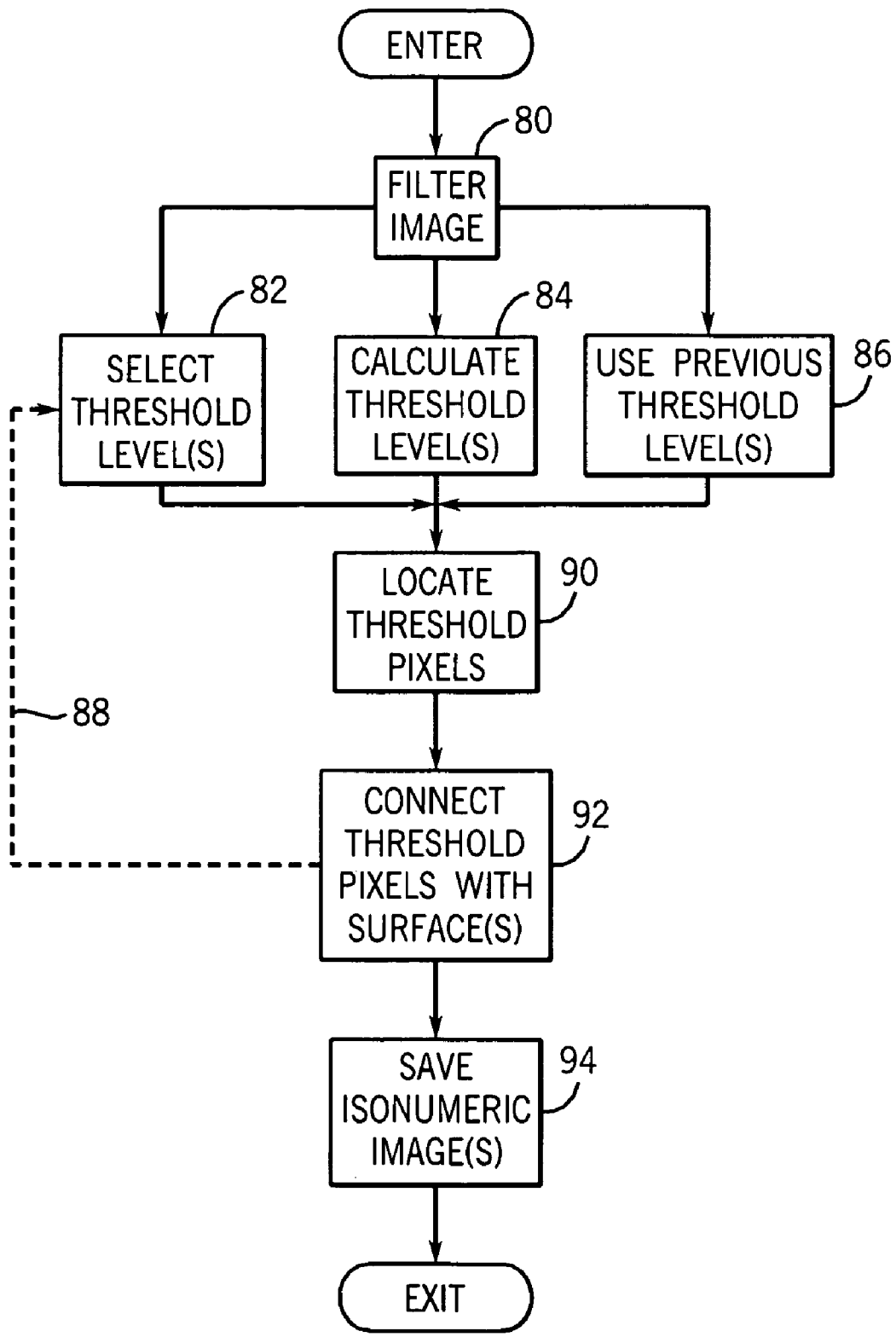
FIG. 3 is a flow chart of the method for producing an isonumeric image which forms part of the software of FIG. 2.

Referring particularly to FIG. 3, the production of an isonumeric image can be accomplished in a number of ways. As indicated at process block 80, most medical images require filtering to improve the results and reduce the processing time. For example, this step gives the user the option of selecting a region in the image for processing rather than processing the entire image. The user draws a line or creates a box around the region containing the tumor, making sure to allow ample space around its boundary.

As indicated by process blocks 82, 84 and 86, one or more threshold levels are then determined. As described above, the threshold level determines the voxels that have a tumor parameter value through which the isonumeric contour is drawn. As indicated at process block 82 this threshold level may be selected manually. For example, with a pancreatic tumor that is imaged with FDG-PET, the tumor boundary level may be set in an iterative process in which different threshold levels are selected and the resulting isonumeric contour is examined to see the relationships between the target (pancreatic tumor) and critical radiosensitive structures, such as the duodenum. This iterative process is indicated in FIG. 3 by dashed line 88.

As indicated by process block 84, the threshold level(s) can also be calculated, based on mathematical or clinical significance related to the diagnostic or therapeutic intervention chosen. Such values can be calculated by examining the acquired image itself, by examining other acquired images, or by using other clinical data such as pathology data or the like. For example, research may determine that a contour delineating the outer border of area within a non-small cell lung cancer that should be "boosted" with stereotactic irradiation, is of no clinical significance for a small-cell lung cancer, due to the much greater radiosensitivity and chemosensitivity of small cell lung cancer, relative to non-small cell lung cancer. Research may show that for non-small cell lung cancer, a "hot" area within a tumor is clinically relevant even if the difference in intensities between the hot area and the rest of the tumor is relatively small. On the other hand, it may be determined that for a hot area to be significant enough to require boost irradiation (and, therefore, automatic contour display) in small cell lung cancer, the difference in threshold values for the hot area versus the rest of the tumor must be much greater, even if the hot area for small cell lung cancer is defined by a contour of minimal spatial or volume difference from adjacent contours.

And finally, as indicated by process block 86, previously determined threshold values(s) may be used. This is normally the case when the current examination is the second or later iteration in the treatment process. In this case the change in the tumor due to the last round of therapy is of paramount importance and the same threshold level(s), normalized if necessary, should be used to measure that change.

After the threshold level(s) has been set, the image data are examined as indicated at process block 90 to locate those voxels at this level(s). This is done by comparing the value of each image voxel with a threshold level and building a separate bit map image in which voxel locations having the threshold level are set to "1" and all other voxels are reset to "0". Rather than a single threshold value, however, a small range of values around the threshold level can be accepted. The size of this range is set to a default value, but it can be adjusted by the operator and the step repeated to obtain the best possible contour. The resulting bit map image(s) will reveal the outline of the tumor at the threshold value. This is repeated for each threshold value such that a bit map image is produced for each. These bit map images are then combined into a single image in which each contour is displayed with a different color to keep them separate.

In many clinical applications the threshold value is compared directly with the image voxel values as described above. However, there are also clinical applications where the image voxel values are processed in some manner before the comparison is made. For example, in multi-slice and 3D magnetic resonance spectroscopic imaging, voxel intensity levels are proportional to molecular concentrations. Isonumeric contours can be created, for which the thresholds chosen represent particular concentrations of a particular molecule. Since studies have shown that ratios of molecular concentration are particularly important in distinguishing tumor from normal tissue, ratios between two molecules for each voxel can be calculated. Isonumeric contours can be created based on the ratios of intensity values (concentrations), rather than the intensity values themselves. In any case, the comparison is made between the selected threshold and voxel values derived from the imported image. It should also be apparent that more than one tumor parameter may be used to produce the isonumeric image. For example, a threshold may be selected from an FDG-PET image indicating a region of high metabolic activity within a tumor, while a threshold may be selected from tumor hypoxia imaging indicating a region of hypoxia. Since the FDG and tumor hypoxia images are registered with each other, these contours can be overlaid upon each other, or upon an anatomic image. These isonumeric contours can also be combined into a single 3D contour for targeting purposes.

Due to a number of factors, including image noise, the bit map image at each threshold will usually not be a continuous 3D surface, but instead, it will show portions of such a surface with missing parts and it will have many disconnected, or stray voxels set to "1". As indicated at process block 92, the next step is to connect "set" voxels to form a continuous 3D surface and reset the stray voxels that are not a part of this surface. This is accomplished by first resetting stray voxels that are disconnected by examining the state of surrounding voxels. If all the voxels surrounding a set voxel are reset, it is considered a stray and it is reset. This filtering is repeated to identify stray groups of 2 through n voxels, where they are surrounded by 2 through n layers respectively of reset voxels. The value of n can be adjusted upward and the step repeated until the stray voxels are removed from the bit map images(s). Then, the remaining set voxels are used in an interpolation process to fill in any missing portions of the 3D contour surface. A cubic spline interpolator is used for this step. As indicated at process block 94, the resulting isonumeric image is then saved in case study storage 56.

It should be noted that more than one isonumeric contour may result from a single threshold applied to a heterogeneous tumor image. This can occur at many different thresholds when the tumor is more in the nature of two side-by-side tumors, but it is more common to see multiple isonumeric contours in a single tumor at a high threshold value. In such cases each isonumeric contour indicates those locations in the tumor where the measured tumor parameter has reached peak values above the threshold.

Since the isonumeric image is derived from the original imported image, it is registered with that image. Therefore, the isonumeric image may be easily merged with the original imported image or any other "anatomic" image or system that is registered therewith.

An important aspect of the system described herein is that it facilitates dynamic administration of cancer treatment. In this context, dynamic means that cancer therapy is administered, the response is assessed, and based on the degree of response or the likelihood of continued response, recommendations are automatically made regarding the next step of treatment. As an example, after images are analyzed, the user is automatically prompted to change the dose of a drug in the next chemotherapy cycle, to change the chemotherapy agents used in the next cycle of chemotherapy, to change the interval between chemotherapy cycles, to proceed to surgery, to perform a more or less extensive surgery, to change the planned radiation therapy dose, to change the radiation therapy fields, to add a stereotactic radiation boost, etc. While the user can independently make treatment-related decisions based on image analysis outcomes, he is also prompted to treat in accordance with image analysis-based recommendations that have been programmed into the system. It is anticipated that if left to make therapeutic decisions on their own based on isonumeric image analyses, oncologists would make decisions that are quite disparate. The automatic prompting of dynamic treatment recommendations will lead to decision-making in accordance with established protocols, will lead to evidence-based decision-making, and will increase the likelihood of consistent decision-making among oncologists.

The invention claimed is:

1. A method for analyzing an image of a tumor, the steps comprising:
   a) selecting a threshold value which is indicative of a parameter of the tumor;
   b) comparing the selected threshold value with values derived from image voxel values;
   c) producing an isonumeric image that depicts a contour of the tumor by setting voxels therein to indicate where in the image the derived image voxel values are substantially the same as the threshold value; and
   d) analyzing the isonumeric image.

2. The method as recited in claim 1 in which the isonumeric image is merged with the image to depict the isonumeric image overlaying anatomic structures depicted in said image.

3. The method as recited in claim 1 in which a plurality of threshold values are selected and compared in steps a) and b) and the isonumeric image depicts a corresponding plurality of contours.

4. The method as recited in claim 1 in which the image is a three-dimensional image and the isonumeric image is a three-dimensional contour.

5. The method as recited in claim 1 in which step a) includes selecting a plurality of threshold values; step b) includes comparing selected threshold values with values derived from image voxel values in different ones of a plurality of images; and step c) includes producing an isonumeric image that depicts a contour corresponding to each selected threshold.

6. The method as recited in claim 5 in which the plurality of images are input from a plurality of different imaging systems and the method includes registering the plurality of images.

7. The method as recited in claim 6 in which the different imaging systems employ different imaging modalities.

8. A dynamic tumor diagnostic and treatment system which comprises:
   means for importing an image of a tumor;
   means for producing from the imported image an isonumeric image which depicts a contour indicative of locations in the imported image having a selected threshold value of a tumor parameter;
   a case study storage for storing isonumeric images; and
   means for analyzing the tumor depicted in the imported image by comparing the isonumeric image produced from the imported image with previously produced isonumeric images stored in the case study storage.

9. The system as recited in claim 8 in which the isonumeric images are three-dimensional images and the means for analyzing includes means for calculating the volume of a contour depicted in an isonumeric image.

10. The system as recited in claim 8 in which the isonumeric images are three-dimensional images and the means for analyzing includes means for calculating the surface area of a contour depicted in an isonumeric image.

11. The system as recited in claim 8 in which the means for producing an isonumeric image includes means for comparing the selected threshold value with values derived from voxel values in the imported image.

12. The system as recited in claim 8 in which includes means for exporting isonumeric images to a therapeutic system.

13. The system as recited in claim 8 which includes:
   means for predicting the outcome of further treatment of the tumor based on the results of the comparison analysis.

14. The system as recited in claim 8 which includes:
   means for indicating further treatment of the tumor based on the results of the comparison analysis.

15. The system as recited in claim 14 in which the means for indicating includes a rules engine that stores a plurality of rules.

16. A dynamic tumor diagnostic and treatment system which comprises:
   means for importing an image of a tumor;
   means for calculating values of parameters that measure the tumor;
   a case study storage for storing the calculated parameters;
   means for analyzing the tumor depicted in the imported image by calculating changes that have occurred in tumor parameters based on parameters previously stored in the case study storage; and
   means for indicating further treatment of the tumor based on a calculated change.

17. The system as recited in claim 16 in which the means for indicating includes a rules engine which stores a plurality of rules that relate changes in a tumor due to prior treatment to a suggested further treatment.

* * * * *

UNITED STATES PATENT AND TRADEMARK OFFICE
CERTIFICATE OF CORRECTION

| | |
|---|---|
| PATENT NO. | : 7,343,030 B2 |
| APPLICATION NO. | : 10/910711 |
| DATED | : March 11, 2008 |
| INVENTOR(S) | : Timothy E. Sawyer |

It is certified that error appears in the above-identified patent and that said Letters Patent is hereby corrected as shown below:

Column 11, claim 1, line 38, "selling" should read --setting--.

Signed and Sealed this

Second Day of September, 2008

JON W. DUDAS
*Director of the United States Patent and Trademark Office*